United States Patent [19]

Duflos et al.

[11] Patent Number: 5,585,390
[45] Date of Patent: Dec. 17, 1996

[54] ALPHA-AMINO ACID COMPOUNDS

[75] Inventors: Muriel Duflos, Saint Pazanne; Sylvie Robert-Piessard; Lucien Welin, both of Nantes; Guillaume Le Baut, Saint Sebastien sur Loire; Daniel-Henri Caignard, Paris; Pierre Renard, Versailles; Gérard Adam, Le Mesnil le Roi, all of France

[73] Assignee: Adir Et Compagnie, Courbevoie, France

[21] Appl. No.: 437,399

[22] Filed: May 9, 1995

Related U.S. Application Data

[62] Division of Ser. No. 268,289, Jun. 30, 1994, Pat. No. 5,470,864.

[30] Foreign Application Priority Data

Jun. 30, 1993 [FR] France .................................. 93 07928

[51] Int. Cl.$^6$ ...................... C07D 213/75; A61K 31/44
[52] U.S. Cl. .............................. 514/64; 514/318; 514/343; 514/352; 546/193; 546/194; 546/309; 546/13; 546/279.1; 546/276.7; 546/278.1; 544/69; 540/541

[58] Field of Search ....................... 546/193, 194, 546/309, 281; 514/318, 343, 352

[56] References Cited

PUBLICATIONS

Sunjic et al, Croatica Chemica Acta, vol. 57, No. 2, 1984, pp. 251–264.
European Search Report for EP 94 40 1267, three pages.
European Patent Application No. 217,286 of Sep. 24, 1986.
Chemical Abstracts Vol. 79, no. 13, 1973, Abstract No. 78046v; pp. 435–436.

Primary Examiner—Zinna Northington Davis
Attorney, Agent, or Firm—The Firm of Gordon W. Hueschen

[57] ABSTRACT

Compounds of the general formula:

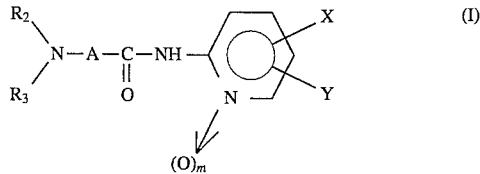

wherein m, X, Y, A, $R_2$ and $R_3$ are defined in the description, and medicaments containing the same.

5 Claims, No Drawings

ALPHA-AMINO ACID COMPOUNDS

The present application is a division of our prior-filed application Ser. No. 08/268,289, filed Jun. 30, 1994, now U.S. Pat. No. 5,470,864.

The present invention relates to new α-amino acid compounds, to a process for the preparation thereof and to pharmaceutical compositions containing them.

A very large number of amino acid compounds are already known.

The Applicants have now discovered that compounds resulting from the coupling of a protected or unprotected α-amino acid with 2-amino-4,6-dimethylpyridine enabled compounds to be obtained that were completely non-toxic and exhibited a high level of anti-inflammatory and/or hypolipaemic properties.

More specifically, the invention relates to compounds of the general formula (I):

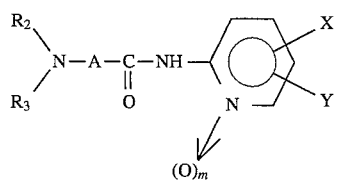

wherein:

m represents 0 or 1, each of X and Y, which may be identical or different, represents an alkyl group, A represents:

1) a group

and $R_1$ represents:
- a hydrogen atom,
- an alkyl group,
- an alkyl group substituted by an amino group,
- an alkylthioalkyl group,
- an alkyl group substituted by an amino grouping that is itself substituted on the amino group by a group selected from tert-butoxycarbonyl, benzyloxycarbonyl and fluorenylmethoxycarbonyl,
- a phenyl or phenylalkyl group,
- a phenyl or phenylalkyl group substituted on the aromatic ring by an alkyl, hydroxy, alkoxy or trifluoromethyl group or by a halogen atom, and in that case—where A represents a —CH($R_1$)—group:

$R_2$ represents a hydrogen atom or $R_2$ forms with $R_1$ and the CH—N grouping carrying them a monocyclic or bicyclic carbon-containing system containing the —CH—N grouping, each ring containing 5 or 6 ring members and being saturated or unsaturated, and $R_3$ represents:
- a hydrogen atom,
- a tert-butoxycarbonyl, benzyloxycarbonyl or fluorenylmethoxycarbonyl group,
- a benzoyl group,
- a benzoyl group substituted by an alkyl, alkoxy, hydroxy or trifluoromethyl group or by a halogen atom, a group

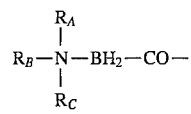

wherein $R_A$, $R_B$ and $R_C$, which may be identical or different, represent a hydrogen atom or an alkyl group, or two groups from among $R_A$, $R_B$ and $R_C$ form with the nitrogen atom carrying them a heterocyclic system selected from pyrrolidine, piperidine, azepine and morpholine, the third group from among $R_A$, $R_B$ and $R_C$ then being either a hydrogen atom or an alkyl group, a group

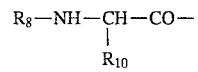

wherein $R_8$ represents hydrogen, tert-butoxycarbonyl, benzyloxycarbonyl or fluorenylmethyloxycarbonyl, glycyl, glycyl itself substituted on the amino group by a group selected from tert.butoxycarbonyl, benzyloxycarbonyl and fluorenylmethoxycarbonyl and $R_{10}$ represents hydrogen; alkyl; alkyl substituted by an amino group; alkyl substituted by an amino group that is itself substituted by a tert-butoxycarbonyl, benzyloxycarbonyl, fluorenylmethyloxycarbonyl; a phenyl group; or phenylalkyl group; or a phenyl or phenylalkyl group substituted on the phenyl ring by an alkyl, hydroxy, alkoxy or trifluoromethyl group or by a halogen atom, 2) a group

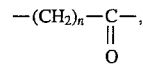

the group

of the radical A being bonded to the group

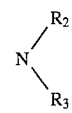

of the compound of formula (I), and n being an integer from 1 to 6 inclusive, and in that case $R_3$ represents a group

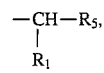

$R_1$ and $R_2$ being as defined above, and $R_5$ representing a B(OH)$_2$, carboxy or alkoxycarbonyl group, or a group

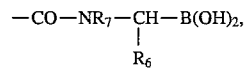

wherein $R_6$ and $R_1$ are identical or different and each is as defined for $R_1$ above, $R_7$ is as defined for $R_2$ above and is identical with or different from $R_2$, their isomers, epimers, enantiomers, diastereoisomers and also their addition salts with a pharmaceutically acceptable acid or base, wherein alkyl and alkoxy are to be understood as being linear or branched groups containing from 1 to 6 carbon atoms.

Of the pharmaceutically acceptable acids that may be added to the compounds of formula (I) to obtain a salt, there may be mentioned by way of non-limiting examples hydrochloric, sulphuric, tartaric, maleic, fumaric, oxalic, methanesulphonic, camphoric acid, etc..

Of the pharmaceutically acceptable bases that may be added to the compounds of formula (I) containing an acid group to obtain a salt, there may be mentioned by way of non-limiting examples, sodium, potassium, calcium and magnesium hydroxide, alkali metal or alkaline earth metal carbonates, or organic bases, such as triethylamine, benzylamine, diethanolamine, tert-butylamine, dicyclohexylamine, arginine, lysine, etc..

Particular embodiments of the invention are:
* compounds having the general formula (I):

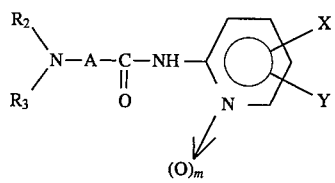

wherein:

m represents 0 or 1, each of X and Y, which may be identical or different, represents an alkyl group, and A represents a group

and $R_1$ represents:
  a hydrogen atom,
  an alkyl group,
  an alkyl group substituted by an amino group,
  an alkylthioalkyl group,
  an alkyl group substituted by an amino grouping that is itself substituted on the amino group by a group selected from tert-butoxycarbonyl, benzyloxycarbonyl and fluorenylmethoxycarbonyl,
  a phenyl or phenylalkyl group,
  a phenyl or phenylalkyl group substituted on the aromatic ring by an alkyl, hydroxy, alkoxy or trifluoromethyl group or by a halogen atom, $R_2$ represents a hydrogen atom or $R_2$ forms with $R_1$ and the CH—N—grouping carrying them a monocyclic or bicyclic carbon-containing system containing the —CH—N—grouping, each ring containing 5 or 6 ring members and being saturated or unsaturated, and $R_3$ represents:
  a hydrogen atom,
  a tert-butoxycarbonyl, benzyloxycarbonyl or fluorenylmethoxycarbonyl group,
  a benzoyl group,
  a benzoyl group substituted by an alkyl, alkoxy, hydroxy or trifluoromethyl group or by a halogen atom, a group

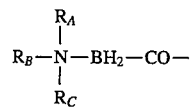

wherein $R_A$, $R_B$, and $R_C$,
  which may be identical or different, represent a hydrogen atom or an alkyl group, or two groups from among $R_A$, $R_B$ and $R_C$ form with the nitrogen atom carrying them a heterocyclic system selected from pyrrolidine, piperidine, azepine and morpholine, the third group from among $R_A$, $R_B$ and $R_C$ then being either a hydrogen atom or an alkyl group, their isomers, epimers, enantiomers, diastereoisomers and also their addition salts with a pharmaceutically acceptable acid or base, wherein alkyl and alkoxy are to be understood as being linear or branched groups containing from 1 to 6 carbon atoms, compounds of the general formula (I):

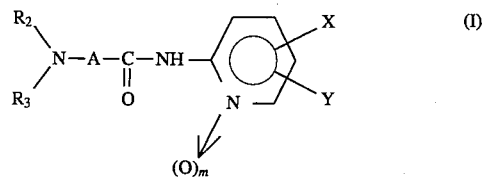

wherein:

m represents 0 or 1, each of X and Y, which may be identical or different, represents an alkyl group and A represents a group

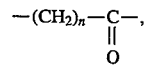

the group

of the radical A being bonded to the group

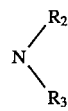

of the compound of formula (I) and n being an integer from 1 to 6 inclusive, $R_3$ represents a group

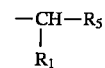

and $R_1$ represents:
  a hydrogen atom,
  an alkyl group,
  an alkyl group substituted by an amino group,
  an alkylthioalkyl group,
  an alkyl group substituted by an amino grouping that is itself substituted on the amino group by a group selected from tert-butoxycarbonyl, benzyloxycarbonyl and fluorenylmethoxycarbonyl, a phenyl or phenylalkyl group,
a phenyl or phenylalkyl group substituted on the aromatic ring by an alkyl, hydroxy, alkoxy or trifluoromethyl group or by a halogen atom, $R_2$ represents a hydrogen atom or $R_2$ forms with $R_1$ and the CH—$NR_3$ grouping carrying them a monocyclic or bicyclic carbon-containing system containing the —CH—N($R_3$) grouping, each ring containing 5 or 6 ring members and being saturated or unsaturated, with $R_5$ representing a B(OH)$_2$, carboxy or alkoxycarbonyl group, or a group

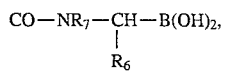

wherein $R_6$ and $R_1$ are identical or different and each is as defined for $R_1$ above, $R_7$ is as defined for $R_2$ above and is identical with or different from $R_2$, their isomers, epimers, enantiomers, diastereoisomers and also their addition salts with a pharmaceutically acceptable acid or base,

* compounds of the general formula I:

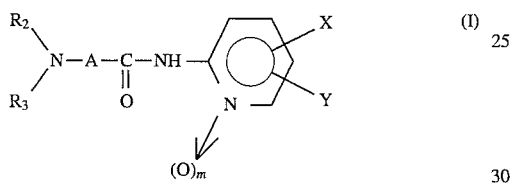

wherein m represents 0 or 1, each of X and Y, which may be identical or different, represents an alkyl group and A represents a group:

and $R_1$ represents:
a hydrogen atom,
an alkyl group substituted by an amino group,
an alkylthioalkyl group,
an alkyl group substituted by an amino grouping that is itself substituted on the amino group by a group selected from tert-butoxycarbonyl, benzyloxycarbonyl and fluorenylmethoxycarbonyl,
a phenyl or phenylalkyl group,
a phenyl or phenylalkyl group substituted on the aromatic ring by an alkyl, hydroxy, alkoxy or trifluoromethyl group or by a halogen atom,
and $R_3$ represents:
a group

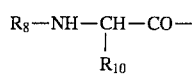

wherein $R_8$ represents hydrogen, tert-butoxycarbonyl, benzyloxycarbonyl or fluorenylmethyloxycarbonyl, glycyl, glycyl substituted on the amino group by a group selected from tert.butoxy carbonyl, benzyloxycarbonyl and fluorenylmethoxycarbonyl and represents hydrogen; alkyl; alkyl substituted by an amino group; alkyl substituted by an amino group that is itself substituted by a tert-butoxycarbonyl, benzyloxycarbonyl, fluorenylmethyloxycarbonyl; a phenyl group or phenylalkyl group; or a phenyl or phenylalkyl group substituted on the phenyl ring by an alkyl, hydroxy, alkoxy or trifluoromethyl group or by a halogen atom, their isomers, epimers, enantiomers, diastereoisomers and also their addition salts with a pharmaceutically acceptable acid or base,

* compounds of formula (I/A):

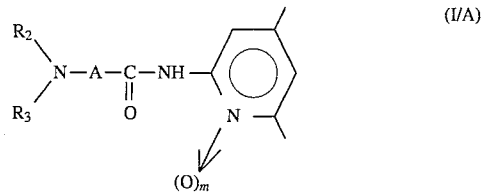

wherein m represents 0 or 1 and A represents a group

and $R_1$ is selected from hydrogen, alkyl and benzyl,
$R_2$ represents hydrogen, benzyloxycarbonyl or tert-butoxycarbonyl and $R_3$ represents:

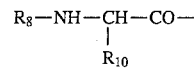

wherein $R_8$ represents hydrogen, tert-butoxycarbonyl, benzyloxycarbonyl or fluorenylmethyloxycarbonyl and $R_{10}$ represents hydrogen; alkyl; alkyl substituted by an amino group; alkyl substituted by an amino group that is itself substituted by a tert-butoxycarbonyl, benzyloxycarbonyl, fluorenylmethyloxycarbonyl; a phenyl group or a phenylalkyl group; or a phenyl or phenylalkyl group substituted on the phenyl ring by an alkyl, hydroxy, alkoxy or trifluoromethyl group or by a halogen atom, their isomers, epimers, enantiomers, diastereoisomers and also their addition salts with a pharmaceutically acceptable acid or base, compounds of formula (I/A)

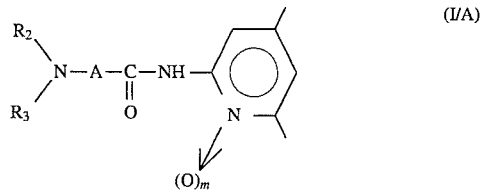

wherein m represents 0 or 1 and A represents a group

and $R_1$ is selected from hydrogen, alkyl and benzyl,
$R_2$ represents hydrogen and $R_3$ represents a group

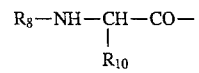

wherein $R_8$ represents hydrogen, tert-butoxycarbonyl, benzyloxycarbonyl or fluorenylmethyloxycarbonyl, glycyl, glycyl substituted on the amino group by a group selected from tert-butoxycarbonyl, benzyloxycarbonyl and fluorenylmethoxycarbonyl and $R_{10}$ represents hydrogen; alkyl; alkyl substituted by an amino group; alkyl substituted by an amino group that is itself substituted by a tert-butoxycarbonyl, benzyloxycarbonyl, fluorenylmethyloxycarbonyl; a phenyl group, or phenylalkyl group; or a phenyl or phenylalkyl group substituted on the phenyl ring by an alkyl, hydroxy, alkoxy or trifluoromethyl group or by a halogen atom, their isomers, epimers, enantiomers, diastereoisomers and also their addition salts with a pharmaceutically acceptable acid or base,

* the compound that is N-2-benzyloxycarbonyl-N-(4,6-dimethylpyridin-2-yl)prolinamide, its N oxide, its isomers and also its addition salts with a pharmaceutically acceptable acid or base,
* the compound that is N-2-benzyloxycarbonyl-N-(4,6-dimethylpyridin-2-yl)glycinamide, its N oxide, and also its addition salts with a pharmaceutically acceptable acid or base,
* the compound that is N-2-(3-fluorobenzoyl)-N-(4,6-dimethylpyridin-2-yl)glycinamide, its N oxide and also its addition salts with a pharmaceutically acceptable acid or base,
* compounds wherein A represents a group:

and $R_3$ represents a group

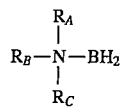

wherein $R_A$, $R_B$ and $R_C$, which may be identical or different, represent a hydrogen atom or an alkyl group, or two groups from among $R_A$, $R_B$ and $R_C$ form with the nitrogen atom carrying them a heterocyclic system selected from pyrrolidine, piperidine, azepine and morpholine, the third group from among $R_A$, $R_B$ and $R_C$ then being either a hydrogen atom or an alkyl group, its N oxide, their isomers and also their addition salts with a pharmaceutically acceptable acid or base,

* the compound that is ethyl N-{4-[N-(4,6-dimethyl-pyridin-2-yl)amino]-1,4-dioxobutyl}glycinate, its N oxide and also its addition salts with a pharmaceutically acceptable acid or base,
* the compound that is {[N-(4,6-dimethylpyridin-2-yl)-2-leucinamido]carbonyl}trimethylaminoboron dihydride, its N oxide, and also its addition salts with a pharmaceutically acceptable acid or base,
* the compound that is N-(4,6-dimethylpyridin-2-yl)glycylglycinamide, its N oxide, and also its addition salts with a pharmaceutically acceptable acid or base,
* the compound that is N(4,6-dimethylpyridin-2-yl)glycylglycylglycinamide, its N oxide, its addition salts with a pharmaceutically acceptable acid or base,
* the compound that is {[N-(4,6-dimethylpyridin-2-yl)-2-methioninamido]carbonyl}trimethylaminoboron dihydride, its N oxide, its isomers and also its addition salts with a pharmaceutically acceptable acid or base,
* the compound that is N-(4,6-dimethylpyridin-2-yl)glycinamide and its N oxide and also its addition salts with a pharmaceutically acceptable acid or base.

The present invention relates also to a process for the preparation of the compounds of formula (I), characterised in that there is used as starting material a compound of formula (II):

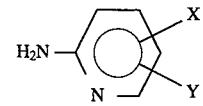

wherein X and Y are as defined above, which is condensed:

* either with a compound of formula (III):

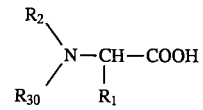

wherein $R_1$ and $R_2$ are as defined in formula (I), and $R_{30}$ represents a tert-butoxycarbonyl, benzyloxycarbonyl or fluorenylmethoxycarbonyl group or

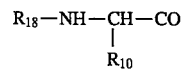

wherein $R_{10}$ is as defined above and $R_{18}$ represents a tert-butoxycarbonyl, benzyloxycarbonyl or fluorenylmethoxycarbonyl group, to yield a compound of formula (IV):

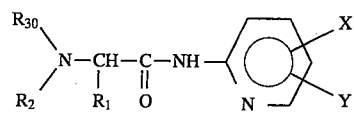

wherein $R_1$, $R_2$, $R_{30}$, X and Y are as defined above, a particular case of the compounds of formula (I) wherein A represents a group

and $R_3$ represents a group $R_{30}$ as defined above, which compound of formula (IV) may then be deprotected to yield a compound of formula (V):

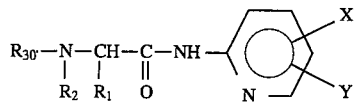

wherein $R_1$, $R_2$, X and Y are as defined above, and $R_{30'}$ is either a hydrogen atom or a group

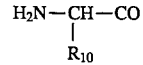

wherein $R_{10}$ is as defined above, a particular case of the compounds of formula (I) wherein $R_3$ represents a group $R_{30'}$ as defined above and A a group

wherein $R_{30'}$, and $R_1$ are as defined above, which compound of formula (V) may, when $R_{30'}$, represents a hydrogen atom, be condensed with a compound of formula (VI):

 (VI), wherein $R_9$ represents:

a phenyl group,
a phenyl group substituted by an alkyl, alkoxy, hydroxy or trifluoromethyl group or by a halogen atom,
a group

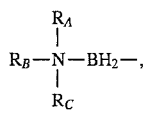

wherein $R_A$, $R_B$ and $R_C$ are as defined above,
a group

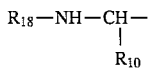

wherein $R_{18}$ represents tert-butoxycarbonyl, benzyloxycarbonyl or fluorenylmethoxycarbonyl or glycyl substituted by tert.butoxycarbonyl, fluorenylmethyloxycarbonyl, or benzyloxy carbonyl, and $R_{10}$ is as defined above, to yield a compound of formula (VII):

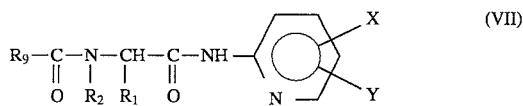

wherein R, $R_2$, $R_9$, X and Y are as defined above, a particular case of the compounds of formula (I) wherein
A represents
a group

and $R_3$ a group —CO—$R_9$
wherein $R_1$ and $R_9$ are as defined above,
which, when $R_9$ represents a group

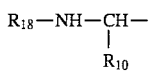

wherein $R_{18}$ and $R_{10}$ being as defined above may, if desired, be subjected to deprotection to yield a compound of formula (XVII)

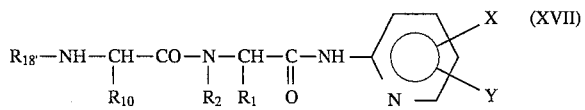

wherein $R_{18'}$ represents a hydrogen atom or a glycyl radical and $R_1$, $R_2$, $R_{10}$, X and Y are as defined above, a particular case of the compounds of formula (I) wherein
A represents a group

and $R_3$ a group

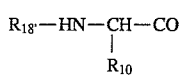

wherein $R_1$, $R_{18'}$ and $R_{10}$ are as defined above,

* or with a compound of formula (VIII):

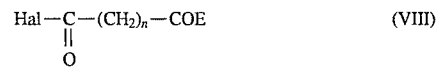

wherein n is as defined above, Hal represents a halogen atom and E represents an alkoxy group, to obtain a compound of formula (IX):

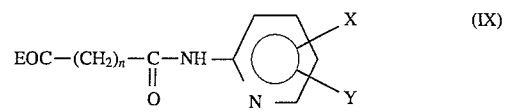

wherein X, Y, n and E are as defined above, which is treated with an alkaline agent to yield a compound of formula (X):

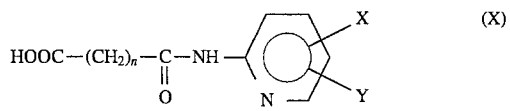

wherein X, Y and n are as defined above, which is treated:
either with a compound of formula (XI):

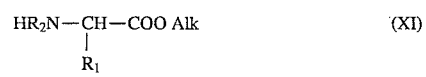

wherein $R_1$ and $R_2$ are as defined above and Alk represents an alkyl group,
to yield a compound of formula (XII):

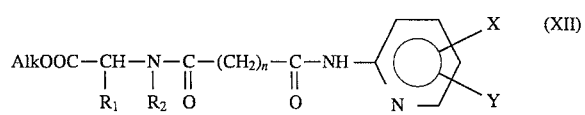

a particular case of a compound of formula (I) wherein
A represents a group $(CH_2)_nCO$ and $R_3$ a group

wherein
$R_5$ represents alkoxycarbonyl and n, $R_1$ and $R_2$ are as defined above,
which compound of formula (XII) is deprotected to yield a compound of formula (XIII):

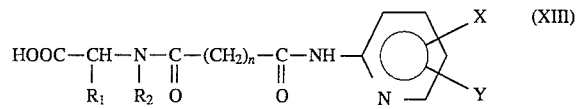

a particular case of the compounds of formula (I) wherein
A represents a group $(CH_2)_nCO$ and $R_3$ a group

wherein
$R_5$ represents a carboxy group, and n, $R_1$ and $R_2$ are as defined above,
which compound of formula (XIII) may be treated with a compound of formula (XIV):

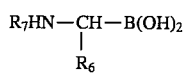 (XIV)

wherein $R_6$ and $R_7$ are as defined in formula (I), which is optionally protected, to yield, where appropriate after deprotection, a compound of formula (XV):

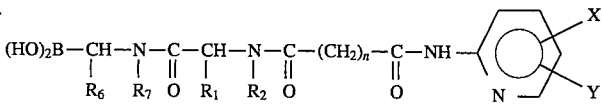 (XV)

a particular case of the compounds of formula (I) wherein represents a group $(CH_2)_nCO$ and $R_3$ a group

wherein
$R_5$ represents a group

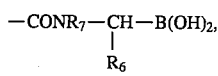

and n, $R_5$, $R_1$, $R_6$ and $R_7$ are as defined in formula (I),
or directly with an optionally protected compound of formula (XIV) to yield, where appropriate after deprotection, a compound of formula (XVI):

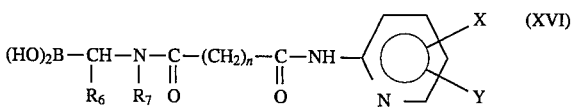 (XVI)

a particular case of a compound of formula (I) wherein
A represents a group

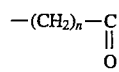

and $R_3$ a group

wherein
$R_5$ represents a group $B(OH)_2$, and $R_6$ is as defined above for $R_1$, and $R_7$ is as defined above for $R_2$,
derivatives of formulae (IV), (V), (VII), (XII), (XIII), (XV), (XVI) and (XVII) that can be, if desired, transformed into the corresponding N oxide of the pyridin system by using hydrogen peroxide,
the isomers of which compounds of formulae (IV), (V), (VII), (XII), (XIII), (XV), (XVI) and (XVII) or their N oxides are optionally separated and which compounds are, if desired, converted into salts using a pharmaceutically acceptable acid or base.

The compounds of formula (I) possess valuable pharmacological properties.

A study of those properties has shown that the compounds of formula (I) are not toxic and exhibit anti-inflammatory, hypolipaemic and diuretic activity.

Because of that activity spectrum, the compounds of the present invention are valuable in various indications, such as inflammatory rheumatism, polyarthritis, rheumatoid arthritis, ankylosing spondylarthritis, arthrosis, articular rheumatism, lumbago, hyperlipaemia, hypertriglyceridaemia and hypercholesterolaemia, and atherosclerosis. In addition, the compounds of the invention are also effective when applied topically, which makes them valuable in various cutaneous indications, such as psoriasis. Finally, owing to their diuretic activity, the compounds of the invention can be used in renal, nephritic, glomerulonephritic and pyelonephritic inflammatory disorders, etc..

The present invention relates also to pharmaceutical compositions containing a compound of formula (I), or one of its addition salts with a pharmaceutically acceptable acid or base, alone or in combination with one or more pharmacologically acceptable excipients.

Of the pharmaceutical compositions according to the invention there may be mentioned more especially, by way of non-limiting examples, those that are suitable for oral, parenteral, nasal, rectal, perlingual, cutaneous, percutaneous, transcutaneous, ocular or pulmonary administration, and especially injectable preparations, aerosols, eye and nose drops, tablets, film-coated tablets and dragées, soft gelatin capsules, hard gelatin capsules, creams, ointments and dermal gels.

The useful dosage varies in accordance with the age and weight of the patient, the mode of administration, the nature of the disorder and any associated treatment, and ranges from 1 mg to 5 g per 24 hours.

The following Examples illustrate the invention and do not limit it in any way.

The starting material is described in the literature or is readily available to the person skilled in the art.

The infrared spectra are produced in a potassium bromide disc containing approximately 1% of the product to be analysed.

STAGE A:

10 mmol of 6-amino-2,4-lutidine are added to a stirred solution of the chosen a-amino acid, which is protected by a benzyloxycarbonyl or tert-butoxycarbonyl group (10 mmol), and carbonyldiimidazole (10 mmol) in anhydrous tetrahydrofuran at ambient temperature. Stirring at ambient temperature is maintained for 10 hours. The solvent is evaporated in vacuo and the residue is purified by chromatography on silica gel using ether as eluant.

Examples 1 to 10 are obtained in that manner. It may be advantageous to replace the carbonyldiimidazole with a phosphine selected from triphenylphosphine and tri-n-butylphosphine in a chlorinated solvent, such as $BrCCl_3$.

EXAMPLE 1

N-2-BENZYLOXYCARBONYL-N-(4,6-DIMETHYLPYRIDIN-2-YL) GLYCINAMIDE ($A=CH_2$: $R_2=H$)

Yield: 77%

Melting point (ether): 103° C.

Spectral characteristics: Infrared: 3220, 1710 and 1670 $cm^{-1}$

EXAMPLE 2

N-2-TERT-BUTOXYCARBONYL-N-(4,6-DIMETHYLPYRIDIN-2-YL) GLYCINAMIDE
($A=CH_2$: $R_2=H$)

Yield: 65%

Melting point (ether): 120° C. Spectral characteristics: Infrared: 3300, 1715 and 1660 $cm^{-1}$

EXAMPLE 3

N-2-BENZYLOXYCARBONYL-N-(4,6-DIMETHYLPYRIDIN-2-YL)ALANINAMIDE

Yield: 70%

Melting point (ether): 121° C. Spectral characteristics: Infrared: 3200, 1715 and 1665 $cm^{-1}$

EXAMPLE 4

N-2-BENZYLOXYCARBONYL-N-(4,6-DIMETHYLPYRIDIN-2-YL)PHENYL ALANINAMIDE

Yield: 60%

Melting point (ether): 139° C. Spectral characteristics: Infrared: 3260, 1705 and 1660 $cm^{-1}$

EXAMPLE 5

N-2-BENZYLOXYCARBONYL-N-(4,6-DIMETHYLPYRIDIN-2-YL) VALINAMIDE

Yield: 73%

Melting point (ether): 134° C. Spectral characteristics: Infrared: 3260, 1710 and 1660 $cm^{-1}$

EXAMPLE 6

N-2-BENZYLOXYCARBONYL-N-(4,6-DIMETHYLPYRIDIN-2-YL)LEUCINAMIDE

Yield: 68% Spectral characteristics: Infrared: 1720 and 1670 $cm^{-1}$

EXAMPLE 7

N-2-BENZYLOXYCARBONYL-N-(4,6-DIMETHYLPYRIDIN-2-YL)ISOLEUCINAMIDE

Yield: 84%

Melting point (ether): 67° C. Spectral characteristics: Infrared: 3260, 1710 and 1665 $cm^{-1}$

EXAMPLE 8

N-2-BENZYLOXYCARBONYL-N-(4,6-DIMETHYLPYRIDIN-2-YL) METHIONINAMIDE

Yield: 87%

Melting point (ether): 70° C. Spectral characteristics: Infrared: 3320, 3200, 1730 and 1660 $cm^{-1}$

EXAMPLE 9

N-2-TERT-BUTOXYCARBONYL-N-(4,6-DIMETHYLPYRIDIN-2-YL) METHIONINAMIDE

Yield: 60%

Melting point (ether): 84° C. Spectral characteristics: Infrared: 3330, 1720 and 1660 $cm^{-1}$

EXAMPLE 10

N-2-BENZYLOXYCARBONYL-N-(4,6-DIMETHYLPYRIDIN-2-YL)PROLINAMIDE

Yield: 73%

Melting point (ether): 149° C. Spectral characteristics: Infrared: 3240, 1705 and 1681 $cm^{-1}$

STAGE B:

The N-2-benzyloxycarbonyl carboxamide compounds obtained in Examples 1, 3, 4, 6 and 7 (100 mmol) are dissolved in methanol, and 0.1 mmol of palladium-on-carbon catalyst(5%) is added. The mixture is stirred at ambient temperature under a hydrogen atmosphere until the absorption of gas ceases. The catalyst is removed by filtration and the filtrate is concentrated in vacuo to give Examples 11 to 15.

EXAMPLE 11

N-(4,6-DIMETHYLPYRIDIN-2-YL)GLYCINAMIDE

Yield: 75%

Melting point: 105° C. Spectral characteristics: Infrared: 3060, 3140 and 1690 $cm^{-1}$

EXAMPLE 12

N-(4,6-DIMETHYLPYRIDIN-2-YL)ALANINAMIDE

Yield: 56% Spectral characteristics: Infrared: 3300, 1670 $cm^{-1}$

EXAMPLE 13

N-(4,6-DIMETHYLPYRIDIN-2-YL) PHENYLALANINAMIDE

Yield: 60%

Melting point: 97° C. (diethyl ether) Spectral characteristics: Infrared: 3240, 1660 $cm^{-1}$

EXAMPLE 14

N-(4,6-DIMETHYLPYRIDIN-2-YL)LEUCINAMIDE

Yield: 55%

Melting point: 78° C. (diethyl ether) Spectral characteristics: Infrared: 3360, 1665 $cm^{-1}$

EXAMPLE 15

N-(4,6-DIMETHYLPYRIDIN-2-YL)ISOLEUCINAMIDE

Yield: 58% Spectral characteristics: Infrared: 3300, 1655 $cm^{-1}$

EXAMPLE 16

N-(4,6-DIMETHYLPYRIDIN-2-YL)METHIONINAMIDE 10 mmol of the product obtained in Example 9 are stirred for one hour in trifluoroacetic acid at ambient temperature. The excess trifluoroacetic acid is evaporated in vacuo to give the trifluoroacetate which is displaced by triethylamine in methylene chloride.

Yield: 60% Spectral characteristics: Infrared: 3240, 1650 cm$^{-1}$

EXAMPLE 17

2-(3-FLUOROBENZOYL)-N'-(4,6-DIMETHYLPYRIDIN-2-YL)GLYCINAMIDE

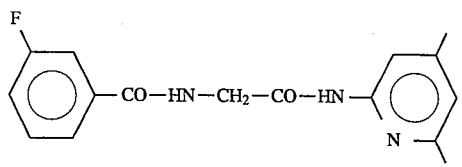

3-fluorobenzoic acid is heated under reflux for one hour in thionyl chloride in the presence of dimethylformamide. The thionyl chloride is removed in vacuo to enable 3-fluorobenzoyl chloride to be obtained. That compound is dissolved in ether, and the solution so obtained is added to a solution of N-(4,6-dimethylpyridin-2-yl)glycinamide obtained in Example 11 in ether, in the presence of triethylamine. The whole is stirred for three hours at ambient temperature. The triethylamine salt is removed by filtration and the solvent is removed by evaporation in vacuo. The residue is purified by chromatography on silica using ether as eluant.

Yield: 53%

Melting point: 161° C. Spectral characteristics: Infrared: 3260, 1680 cm$^{-1}$

EXAMPLE 18

{[N-(4,6-DIMETHYLPYRIDIN-2-YL)-2-GLYCINAMIDO]CARBONYL} TRIMETHYLAMINOBORON DIHYDRIDE

By using the couple P (Ph)$_3$/CCl$_4$ in the presence of (carboxy)(trimethylamino)boron dihydride on the compound of Example 11, there is obtained in accordance with SPIELVOGEL et al. (J. Am. Chem. Soc. 1976, 100, 5702–5703) the title product which has the formula:

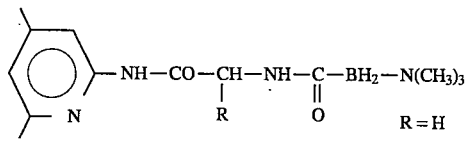

Yield: 48% Melting point: 106° C.

By proceeding exactly as in Examples 13, 14 and 16, there are obtained:

EXAMPLE 19

{[N-(4,6-DIMETHYLPYRIDIN-2-YL)-2-PHENYLALANINAMIDO]CARBONYL}-TRIMETHYLAMINOBORON DIHYDRIDE
(R=benzyl)

Yield: 51%

Melting point: 82° C.

EXAMPLE 20

{[N-(4,6-DIMETHYLPYRIDIN-2-YL)-2-LEUCINAMIDO]CARBONYL}-TRIMETHYLAMINOBORON DIHYDRIDE
(R=CH$_2$—CH(CH$_3$)$_2$)

Yield: 45%, oil

EXAMPLE 21

{[N-(4,6-DIMETHYLPYRIDIN-2-YL)-2-METHIONINAMIDO]CARBONYL}-TRIMETHYLAMINOBORON DIHYDRIDE
(R=—CH$_2$CH$_2$—S—CH$_3$)

Yield: 46%

Melting point: 120° C.

EXAMPLE 22

{[N-(4,6-DIMETHYLPYRIDIN-2-YL)-2-GLYCINAMIDO]CARBONYL}-N-METHYLPIPERIDINOBORON DIHYDRIDE

By proceeding as in Example 18, but replacing the (carboxy)(trimethylamino)boron dihydride with carboxy-N-(methylpiperidino)boron dihydride, the title product is obtained.

Yield: 58%

Melting point: 140° C.

EXAMPLE 23

ETHYL N-{4-{[(4,6-DIMETHYLPYRIDIN-2-YL)AMINO]-1,4-DIOXO}BUTYL}GLYCINATE

STAGE A:

100 mmol of 6-amino-2,4-lutidine and 100 mmol of 4-chloro-4-oxobutanoic acid ethyl ester are reacted in methylene chloride in the presence of triethylamine. The salt formed is filtered off, the reaction medium is evaporated and the 4-(4,6-dimethylpyridin-2-yl)amino-4-oxobutanoic acid ethyl ester is purified on silica gel.

STAGE B:

10 mmol of the product obtained in stage A are stirred for one hour in 0.1N sodium hydroxide solution. By the slow addition of a weak acid, 4-(4,6-dimethylpyridin-2-yl)amino-4-oxobutanoic acid precipitates.

STAGE C:

The 4-(4,6-dimethylpyridin-2-yl)amino-4-oxobutanoic acid is condensed with ethyl glycinate in the presence of triphenylphosphine in a mixture of trichlorobromomethane and tetrahydrofuran to obtain the title product.

EXAMPLE 24

BENZYLOXYCARBONYL-N-(4,6-DIMETHYLPYRIDIN-2-YL) GLYCYLGLYCINAMIDE 2 g of benzyloxycarbonylglycine are dissolved in 30 ml of dry tetrahydrofuran. Carbonyldiimidazole (1.62 g, 10 mmol) are added. The whole is stirred for 1 hour at ambient temperature before adding the product of Example 11 (1.80 10 mmol). After stirring for 6 hours at ambient temperature, the title product is filtered off and washed with THF.

EXAMPLE 25

N-(4,6-DIMETHYLPYRIDIN-2-YL)GLYCINAMIDE 1 g (2.6 mmol) of the product of Example 24 is dissolved in 60 ml of methanol. Palladium-on-carbon is added and the whole is stirred under a hydrogen atmosphere. Filtration is then carried out, the methanol is evaporated and the title product is recovered.

Melting point: decomposition above 180° C. Spectral characteristics: $^1$H NMR 3.99 ppm singlet 2H ($\underline{CH}_2$ NH)

EXAMPLE 26

N-(4,6-DIMETHYLPYRIDIN-2-YL)GLYCYLGLYCYL CLYCINAMIDE 10 mmol of N-(4,6-dimethylpyridin-2-yl)glycinamide obtained as disclosed in example 11 are added to a stirred solution of benzyloxycarbonylglycylglycine (10 mmoles) and carbonyldiimidazole (10 mmoles) in anhydrous tetrahydrofuran at ambient temperature. Stirring at ambient temperature is maintained for 10 hours. The solvent is evaporated in vacuo and the residue is purified by chromatography on silica gel using ether as eluant.

EXAMPLE 27

N-(4,6-DIMETHYLPYRIDIN-2-YL)GLYCINAMIDE N OXIDE 1 g of compound disclosed in example 11 is added to a stirred solution of 10 ml of glacial acetic acid and 0.7 ml of hydrogen peroxide (35%). The reactional medium is treated at 70° C. for 7 hours. The solvent is evaporated in vacuo at a reduce temperature. Filter and wash with iced water. The title compound is purified by column chromatography and recrystallized.

PHARMACOLOGICAL STUDY OF THE COMPOUNDS OF THE INVENTION

EXAMPLE 28

ACUTE TOXICITY STUDY

Acute toxicity was evaluated after the oral administration to groups of 8 mice (26±2 grams) of a dose of 650 mg.kg$^{-1}$. The animals were observed at regular intervals in the course of the first day and daily during the 2 weeks following treatment.

It appears that the compounds of the invention are completely non-toxic. No death is observed after the administration of a dose of 650 mg.kg$^{-1}$. No disorders are observed after the administration of that dose.

EXAMPLE 29

STUDY OF ANTI-INFLAMMATORY ACTIVITY

The method used is that of the carrageenin plantar oedema. The protocol used is the following: the compounds of the invention are administered intraperitoneally at a dose of 100 mg.kg$^{-1}$ in a 0.05% suspension in a mixture of Tween 80 and water to male CF1 mice of an average weight of 25 g. The administration is carried out in the sole of the right paw for 3 hours and then again 30 minutes before the injection of 0.2 ml of a 9% saline solution of 1% carrageenin. The saline solution is also injected into the sole of the left paw which acts as a control. Three hours later, the two paws are cut off at the tibiotarsal joint in accordance with Winter's modified method (J. Pharmacol. Exp. Ther. 1970, 175,435–442 and Clin. Chim. Acta 10, 229–237).

The weight of the left paw increases by 78±3 mg. The weight of the right paw does not increase, owing to the complete efficacy of the products of the invention.

EXAMPLE 30

HYPOLIPAEMIC ACTIVITY

Male CF1 mice of an average weight of 28 g are treated intraperitoneally for 16 days with the products of the invention (in 1% suspension in carboxymethylcellulose) at the rate of 20 mg/kg per day. On days 9 and 16, a blood sample is taken from the animals. The plasma is obtained by centrifugation (3 min×3000 g). The total cholesterol is determined by the Liebermann-Buchard reaction (Clin. Chim. Acta, 1964, 10, 229–237) and the triglycerides are determined using a commercial kit (Bio Dynamics/bmc triglyceride kit). The products of the invention administered intraperitoneally at the rate of 20 mg.kg$^{-1}$ per day permit a reduction of approximately 70% in cholesterol and plasmic triglycerides.

EXAMPLE 31

STUDY OF DIURETIC ACTIVITY

Groups of 3 rats that have not been fed are used. Each group receives 25 ml/kg p.o. of distilled water administered with the products of the invention (30 mg/kg). The volume of urine is measured for the 6 hours following administration. The diuretic activity of the products of the invention is comparable to that of furosemide used as a reference.

EXAMPLE 32

PHARMACEUTICAL COMPOSITIONS

Tablets for the treatment of inflammatory disorders Tablets each containing 10 mg of N-(4,6-dimethylpyridin2-yl)glycylglycinamide

| Preparation formula for 1000 tablets | |
|---|---|
| N-(4,6-dimethylpyridin-2-yl)glycylglycinamide | 10 g |
| wheat starch | 35 g |
| corn starch | 65 g |
| lactose | 65 g |
| magnesium stearate | 2 g |
| silica | 1 g |
| hydroxypropylcellulose | 2 g |

Tablets for the treatment of hypercholesterolaemia and hypertriglyceridaemia each containing 15 mg of {[4,6-dimethylpyridin-2-yl)-2-(phenylalaninamido)carbonyl]}-trimethylaminoboron dihydride

| Preparation formula for 1000 tablets | |
|---|---|
| {[4,6-dimethylpyridin-2-yl)-2-(phenylalaninamido) carbonyl]}trimethylaminoboron dihydride | 15 g |
| wheat starch | 35 g |
| corn starch | 65 g |
| lactose | 65 g |
| magnesium stearate | 2 g |
| silica | 1 g |
| hydroxypropylcellulose | 2 g |

Ointment for the treatment of psoriasis containing 1% N-(4,6-dimethylpyridin-2-yl)glycylglycinamide

| Preparation formula for 1000 kilograms | |
|---|---|
| N-(4,6-dimethylpyridin-2-yl)glycylglycinamide | 1 kg |
| Excipients qsp<br>(Cetyl alcohol, stearyl alcohol, isopropyl alcohol, lanolin, polyethylene glycol monostearate, distilled aqua laurocerasi.) | 1000 kg |

We claim:

1. A compound selected from those of the formula (I):

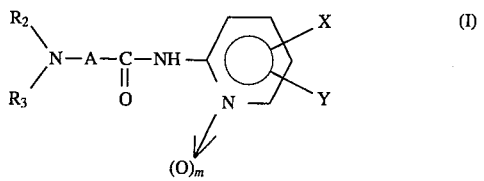

wherein:

m is 0 or 1, each of X and Y, which may be identical or different, represents an alkyl group, and $R_1$ represents:
- a hydrogen atom,
- an alkyl group,
- an alkyl group substituted by an amino group,
- an alkylthioalkyl group,
- an alkyl group substituted by an amino group that is itself substituted on the amino group by a group selected from tert-butoxycarbonyl, benzyloxycarbonyl and fluorenylmethoxycarbonyl,
- a phenyl or phenylalkyl group,
- a phenyl or phenylalkyl group substituted on the aromatic ring by an alkyl, hydroxy, alkoxy or trifluoromethyl group or by a halogen atom, $R_2$ represents a hydrogen atom or $R_2$ forms with $R_1$ and the

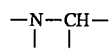

grouping carrying them a monocyclic or bicyclic ring system, each ring containing 5 or 6 ring members and being saturated or unsaturated, A represents a group —(CH$_2$)$_n$

the group —CO— of the radical A being bonded to the group

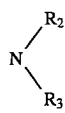

of the compound of formula (I), and n being an integer of 1 to 6 inclusive, $R_3$ represents a group

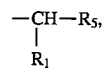

$R_1$ and $R_2$ being as defined above, and $R_5$ representing a $B(OH)_2$, carboxy or alkoxycarbonyl group, or a group

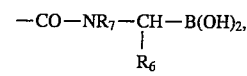

wherein $R_6$ and $R_1$ are identical or different and each is as defined for $R_1$ above, $R_7$ is as defined for $R_2$ above and is identical with or different from $R_2$, their isomers, epimers, enantiomers, diastereoisomers and also their addition salts with a pharmaceutically-acceptable acid or base, wherein alkyl and alkoxy are linear or branched groups containing 1 to 6 carbon atoms inclusive.

2. A compound as claimed in claim 1 selected from those of the formula (I):

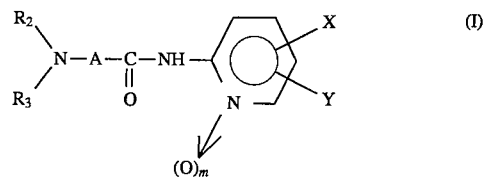

wherein:

m represents 0 or 1, each of X and Y, which may be identical or different, represents an alkyl group and A represents a group —(CH$_2$)$_n$

the group —CO— of the radical A being bonded to the group

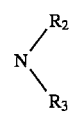

of the compound of formula (I) and n being an integer of 1 to 6 inclusive, $R_3$ represents a group

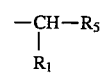

and $R_1$ represents:
- a hydrogen atom,
- an alkyl group,
- an alkyl group substituted by an amino group,
- an alkylthioalkyl group, an alkyl group substituted by an amino group that is itself substituted on the amino group by a group selected from tert-butoxycarbonyl, benzyloxycarbonyl and fluorenylmethoxycarbonyl, a phenyl or phenylalkyl group, a phenyl or phenylalkyl group substituted on the aromatic ring by an alkyl, hydroxy, alkoxy or trifluoromethyl group or by a halogen atom, $R_2$ represents a hydrogen atom or $R_2$ forms with $R_1$ and the

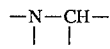

grouping carrying them a monocyclic or bicyclic ring system, each ring containing 5 or 6 ring members and being saturated or unsaturated, with $R_5$ representing a $B(OH)_2$, carboxy or alkoxycarbonyl group, or a group

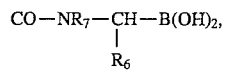

wherein $R_6$ and $R_1$ are identical or different and each is as defined for $R_1$ above, $R_7$ is as defined for $R_2$ above and is identical with or different from $R_2$, their isomers, epimers, enantiomers, diastereoisomers and also their addition salts with a pharmaceutically-acceptable acid or base.

3. A compound as claimed in claim 1 selected from ethyl N-{[1,4-dioxo-4-(4,6-dimethylpyridin-2-yl)amino]butyl}glycinate, and its N oxide, and its addition salts with a pharmaceutically-acceptable acid or base.

4. A pharmaceutical composition containing as active ingredient a compound according to claim 1 in combination with one or more pharmaceutically-acceptable excipients or carriers.

5. A method for treating a living animal afflicted with a condition selected from an inflammatory disorder, hypercholesterolaemia, hypertriglyceridaemia, or psoriasis, comprising the step of administering to the said living animal an amount of a compound of claim 1 which is effective for the alleviation of the said condition.

* * * * *

UNITED STATES PATENT AND TRADEMARK OFFICE
CERTIFICATE OF CORRECTION

PATENT NO. : 5,585,390
DATED : December 17, 1996           Page 1 of 2
INVENTOR(S) : M. Duflos, S. Robert-Piessard; L. Welin; G. Le Baut; D. Caignard; P. Renard; G. Adam It is certified that error appears in the above-indentified patent and that said Letters Patent is hereby corrected as shown below:

Column 5, line 62: Insert -- $R_{10}$ -- at the beginning of the line.

Column 8, line 46: In the first line below the formula, "$R_{30},$" should read -- $R_{30'}$ -- (the comma should be a prime).

Column 8, line 55: "$R_{30},$" should read -- $R_{30'}$ -- (the comma should be a prime).

Column 8, line 60: "$R_{30},$" should read -- $R_{30'}$ -- (the comma should be a prime).

Column 8, line 61: "$R_{30},$" should read -- $R_{30'}$ -- (the comma should be a prime).

Column 9, line 52: In the first line below the formula, "$R_{18},$" should read -- $R_{18'}$ --.

Column 9, line 67: In the first line below the formula, "$R_{18},$" should read -- $R_{18'}$ --.

Column 11, line 15 (approx.): "represents" should read -- A represents --.

Column 12, line 44: "a-amino" should read -- α-amino --.

UNITED STATES PATENT AND TRADEMARK OFFICE
CERTIFICATE OF CORRECTION

PATENT NO. : 5,585,390
DATED : December 17, 1996
INVENTOR(S) : M. Duflos, S. Robert-Piessard; L. Welin; G. Le Baut; D. Caignard; P. Renard; G. Adam It is certified that error appears in the above-indentified patent and that said Letters Patent is hereby corrected as shown below:

Column 17, line 29: "CLYCINAMIDE" should read -- GLYCINAMIDE --.

Column 18, line 53: "Tablets each containing....." should start a new paragraph.

Column 19, line 51: Insert "and" at the beginning of the line befor "$R_2$".

Column 19, line 60: Insert "and" at the beginning of the line before "A".

Signed and Sealed this

Fifteenth Day of April, 1997

Attest:

BRUCE LEHMAN

Attesting Officer            Commissioner of Patents and Trademarks